United States Patent
Salo et al.

(10) Patent No.: US 7,869,871 B2
(45) Date of Patent: Jan. 11, 2011

(54) PACING THERAPY FOR DIASTOLIC HEART FAILURE

(75) Inventors: Rodney W. Salo, Fridley, MN (US); Guy Alvarez, Lino Lakes, MN (US); Eric G. Lovett, Mendota Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 610 days.

(21) Appl. No.: 11/278,330

(22) Filed: Mar. 31, 2006

(65) Prior Publication Data

US 2007/0239219 A1  Oct. 11, 2007

(51) Int. Cl.
A61N 1/00 (2006.01)

(52) U.S. Cl. ......................................... 607/9

(58) Field of Classification Search ............ 607/9, 607/32; 600/486
See application file for complete search history.

(56) References Cited

U.S. PATENT DOCUMENTS

| | | | |
|---|---|---|---|
| 3,995,623 A | 12/1976 | Blake et al. | |
| 4,354,497 A | 10/1982 | Kahn | |
| 4,401,119 A | 8/1983 | Herpers | |
| 4,432,362 A | 2/1984 | Leckrone et al. | |
| 4,485,813 A | 12/1984 | Anderson et al. | |
| 4,674,518 A | 6/1987 | Salo | |
| 4,686,987 A | 8/1987 | Salo et al. | |
| 4,719,921 A | 1/1988 | Chirife | |
| 4,872,459 A | 10/1989 | Pless et al. | |
| 4,880,005 A | 11/1989 | Pless et al. | |
| 4,922,907 A | 5/1990 | Hedin et al. | |
| 4,928,688 A | 5/1990 | Mower | |
| 4,945,909 A | 8/1990 | Fearnot et al. | |
| 5,014,698 A | 5/1991 | Cohen | |
| 5,083,563 A | 1/1992 | Collins | |
| 5,129,394 A * | 7/1992 | Mehra | 607/23 |
| 5,156,149 A | 10/1992 | Hudrlik | |
| 5,158,079 A | 10/1992 | Adams et al. | |
| 5,163,429 A | 11/1992 | Cohen | |
| 5,168,869 A | 12/1992 | Chirife | |

(Continued)

FOREIGN PATENT DOCUMENTS

EP  0474958 A2  3/1992

(Continued)

OTHER PUBLICATIONS

"U.S. Appl. No. 10/703,398, Advisory Action mailed Jul. 17, 2008", 5 pgs.

(Continued)

Primary Examiner—George Manuel
Assistant Examiner—Robert N Wieland
(74) Attorney, Agent, or Firm—Schwegman, Lundberg & Woessner, P.A.

(57) ABSTRACT

Described herein are methods and systems for delivering pacing therapy to HF patients who do not exhibit a reduced EF. Such patients do not have systolic dysfunction and generally do not benefit from established HF therapies that either augment contractile function or counteract conduction abnormalities. In one embodiment, a HF patient with a normal EF is tested for the adequacy of heart rate response during exercise. If the patient is found to be chronotropically incompetent, a rate-adaptive pacing mode is employed in order to improve functional capacity.

35 Claims, 4 Drawing Sheets

U.S. PATENT DOCUMENTS

| | | | |
|---|---|---|---|
| 5,174,289 A | 12/1992 | Cohen | |
| 5,179,949 A | 1/1993 | Chirife | |
| 5,188,106 A * | 2/1993 | Nappholz et al. | 607/24 |
| 5,233,985 A | 8/1993 | Hudrlik | |
| 5,267,560 A | 12/1993 | Cohen | |
| 5,271,395 A * | 12/1993 | Wahlstrand et al. | 607/9 |
| 5,318,595 A | 6/1994 | Ferek-Petric et al. | |
| 5,324,326 A | 6/1994 | Lubin | |
| 5,330,511 A | 7/1994 | Boute | |
| 5,334,222 A * | 8/1994 | Salo et al. | 607/17 |
| 5,368,040 A * | 11/1994 | Carney | 600/513 |
| 5,370,665 A | 12/1994 | Hudrlik | |
| 5,372,607 A | 12/1994 | Stone et al. | |
| 5,417,717 A * | 5/1995 | Salo et al. | 607/18 |
| 5,433,205 A * | 7/1995 | Visveshwara | 600/455 |
| 5,464,434 A | 11/1995 | Alt | |
| 5,514,161 A | 5/1996 | Limousin | |
| 5,514,163 A | 5/1996 | Markowitz et al. | |
| 5,527,347 A | 6/1996 | Shelton et al. | |
| 5,534,016 A | 7/1996 | Boute | |
| 5,549,650 A | 8/1996 | Bornzin et al. | |
| 5,554,177 A | 9/1996 | Kieval et al. | |
| 5,584,867 A | 12/1996 | Limousin et al. | |
| 5,584,868 A | 12/1996 | Salo et al. | |
| 5,609,612 A | 3/1997 | Plicchi et al. | |
| 5,626,620 A | 5/1997 | Kieval et al. | |
| 5,626,623 A | 5/1997 | Kieval et al. | |
| 5,628,777 A | 5/1997 | Moberg et al. | |
| 5,674,259 A | 10/1997 | Gray | |
| 5,683,429 A | 11/1997 | Mehra | |
| 5,690,689 A | 11/1997 | Sholder | |
| 5,700,283 A | 12/1997 | Salo | |
| 5,713,930 A | 2/1998 | van der Veen et al. | |
| 5,716,383 A | 2/1998 | Kieval et al. | |
| 5,728,140 A | 3/1998 | Salo et al. | |
| 5,749,906 A | 5/1998 | Kieval et al. | |
| 5,755,766 A | 5/1998 | Chastain et al. | |
| 5,797,970 A | 8/1998 | Pouvreau | |
| 5,800,471 A | 9/1998 | Baumann | |
| 5,824,019 A | 10/1998 | Rueter et al. | |
| 5,935,160 A | 8/1999 | Auricchio et al. | |
| 6,038,483 A | 3/2000 | KenKnight et al. | |
| 6,044,298 A | 3/2000 | Salo et al. | |
| 6,058,329 A | 5/2000 | Salo et al. | |
| 6,108,577 A | 8/2000 | Benser | |
| 6,112,117 A | 8/2000 | KenKnight et al. | |
| 6,128,534 A * | 10/2000 | Park et al. | 607/17 |
| 6,136,021 A | 10/2000 | Tockman et al. | |
| 6,144,880 A | 11/2000 | Ding et al. | |
| 6,151,524 A | 11/2000 | Krig et al. | |
| 6,152,955 A | 11/2000 | KenKnight et al. | |
| 6,198,952 B1 | 3/2001 | Miesel | |
| 6,208,901 B1 | 3/2001 | Hartung | |
| 6,223,082 B1 | 4/2001 | Bakels et al. | |
| 6,273,856 B1 | 8/2001 | Sun et al. | |
| 6,280,389 B1 | 8/2001 | Ding et al. | |
| 6,309,350 B1 | 10/2001 | VanTassel et al. | |
| 6,311,089 B1 | 10/2001 | Mann et al. | |
| 6,314,322 B1 | 11/2001 | Rosenberg | |
| 6,351,673 B1 | 2/2002 | Ding et al. | |
| 6,360,127 B1 | 3/2002 | Ding et al. | |
| 6,398,738 B1 | 6/2002 | Millar | |
| 6,411,848 B2 * | 6/2002 | Kramer et al. | 607/9 |
| 6,418,346 B1 | 7/2002 | Nelson et al. | |
| 6,430,439 B1 | 8/2002 | Wentkowski et al. | |
| 6,438,421 B1 | 8/2002 | Stahmann et al. | |
| 6,449,510 B1 | 9/2002 | Albers et al. | |
| 6,480,742 B2 | 11/2002 | Stahmann et al. | |
| 6,507,756 B1 | 1/2003 | Heynen et al. | |
| 6,512,952 B2 | 1/2003 | Stahmann et al. | |
| 6,522,921 B2 | 2/2003 | Stahmann et al. | |
| 6,522,923 B1 | 2/2003 | Turcott | |
| 6,542,775 B2 | 4/2003 | Ding et al. | |
| 6,553,258 B2 | 4/2003 | Stahmann et al. | |
| 6,597,951 B2 | 7/2003 | Kramer et al. | |
| 6,628,988 B2 * | 9/2003 | Kramer et al. | 607/9 |
| 6,654,637 B2 | 11/2003 | Rouw et al. | |
| 6,666,826 B2 | 12/2003 | Salo et al. | |
| 6,684,103 B2 | 1/2004 | Ding et al. | |
| 6,754,532 B1 | 6/2004 | Ferek-Petric | |
| 6,795,732 B2 | 9/2004 | Stadler et al. | |
| 6,810,284 B1 * | 10/2004 | Bradley | 600/510 |
| 6,832,113 B2 | 12/2004 | Belalcazar | |
| 6,839,593 B1 * | 1/2005 | Sun et al. | 607/17 |
| 6,856,836 B2 | 2/2005 | Ding et al. | |
| 6,859,665 B2 | 2/2005 | Ding et al. | |
| 6,892,095 B2 | 5/2005 | Salo | |
| 6,970,742 B2 * | 11/2005 | Mann et al. | 607/23 |
| 7,024,244 B2 * | 4/2006 | Muhlenberg et al. | 607/23 |
| 7,037,266 B2 * | 5/2006 | Ferek-Petric et al. | 600/453 |
| 7,092,759 B2 | 8/2006 | Nehls et al. | |
| 2001/0047194 A1 | 11/2001 | Thompson et al. | |
| 2002/0002389 A1 | 1/2002 | Bradley et al. | |
| 2002/0123769 A1 | 9/2002 | Panken et al. | |
| 2002/0151938 A1 | 10/2002 | Corbucci | |
| 2003/0055345 A1 * | 3/2003 | Eigler et al. | 600/486 |
| 2003/0074029 A1 * | 4/2003 | Deno et al. | 607/23 |
| 2003/0078628 A1 | 4/2003 | Holmstrom et al. | |
| 2003/0105496 A1 | 6/2003 | Yu et al. | |
| 2003/0120319 A1 * | 6/2003 | Sun et al. | 607/17 |
| 2003/0130581 A1 | 7/2003 | Salo et al. | |
| 2003/0144702 A1 | 7/2003 | Yu et al. | |
| 2003/0144703 A1 | 7/2003 | Yu et al. | |
| 2004/0015081 A1 | 1/2004 | Kramer et al. | |
| 2004/0019365 A1 | 1/2004 | Ding et al. | |
| 2004/0147966 A1 | 7/2004 | Ding et al. | |
| 2004/0193223 A1 | 9/2004 | Kramer et al. | |
| 2005/0038477 A1 | 2/2005 | Kramer et al. | |
| 2005/0102002 A1 | 5/2005 | Salo et al. | |
| 2005/0115561 A1 * | 6/2005 | Stahmann et al. | 128/200.24 |
| 2006/0089679 A1 * | 4/2006 | Zhu et al. | 607/32 |

FOREIGN PATENT DOCUMENTS

| | | |
|---|---|---|
| EP | 0970721 A2 | 1/2000 |
| WO | WO-99/10042 A1 | 3/1999 |
| WO | WO-99/58191 A1 | 11/1999 |
| WO | WO-01/76689 A2 | 10/2001 |
| WO | WO-02/087693 A2 | 11/2002 |
| WO | WO-02/087694 A1 | 11/2002 |
| WO | WO-03/041797 A2 | 5/2003 |
| WO | WO-2004/011088 A1 | 2/2004 |
| WO | WO-2004/069333 A2 | 8/2004 |
| WO | WO 2005/046788 A2 | 5/2005 |
| WO | WO 2007/115188 A2 | 10/2007 |

OTHER PUBLICATIONS

"U.S. Appl. No. 10/703,398, Advisory Action mailed Aug. 14, 2008", 3 pgs.

"U.S. Appl. No. 10/703,398, Final Office Action mailed May 7, 2007", 10 pgs.

"U.S. Appl. No. 10/703,398, Non-Final Office Action mailed Jan. 25, 2007", 12 pgs.

"U.S. Appl. No. 10/703,398, Response filed Jan. 19, 2008 to Non-Final Office Action mailed Nov. 19, 2007", 20 pgs.

"U.S. Appl. No. 10/703,398, Response filed Apr. 20, 2007 to Non-Final Office Action mailed Jan. 25, 2007", 21 pgs.

"U.S. Appl. No. 10/703,398, Response filed Jun. 30, 2008 to Final Office Action mailed Apr. 29, 2008", 21 pgs.

"U.S. Appl. No. 10/703,398, Response filed Jul. 31, 2007 to Final Office Action mailed May 7, 2007", 18 pgs.

"U.S. Appl. No. 10/703,398, Non-Final Office Action mailed Dec. 10, 2008", 11 pgs.

"U.S. Appl. No. 10/703,398, Non-Final Office Action mailed Nov. 19, 2007", 10 pgs.

"U.S. Appl. No. 10/703,398, Response filed Aug. 29, 2008 to Final Office Action mailed Apr. 29, 2008 and the Advisory Action mailed Jul. 17, 2008", 22 pgs.

"U.S. Appl. No. 10/703,398, Final Office Action mailed Apr. 29, 2008", 11 pgs.

"U.S. Appl. No. 10/703,398, Response filed Apr. 9, 2009 to Non Final Office Action mailed Dec. 10, 2008", 22 pgs.

"International Application Serial No. PCT/US2004/037129, International Search Report mailed Mar. 15, 2005", 4 pgs.

International Application Serial No. PCT/US2004/037129, Written Opinion mailed Mar. 15, 2005, 6 pgs.

Auricchio, A, "The Pacing Therapies for Congestive Heart Failure (PATH-CHF) Study: Rationale, Design, and Endpoints of a Prospective Radomized Multicenter Study", *The American Journal of Cardiology*, 83(5B), (1999), 130D-135D.

Auricchio, A., "Effect of Pacing Chamber and Atrioventricular Delay on Acute Systolic Function of Paced Patients With Congestive Heart Failure", *Circulation* 99(23), (Jun. 15, 1999), 2993-3001.

Breithardt, Ole A, "Acute effects of cardiac resynchronization therapy on left ventricular Doppler indices in patients with congestive heart failure", *American Heart Journal*, vol. 143, No. 1, (Jan. 2002), 34-44.

Breithardt, Ole A., "Echocardiographic Quantification of Left Ventricular Asynchrony Predicts an Acute Hemodynamic Benefit of Cardiac Resynchronization Therapy", *Journal of the American College of Cardiology*, vol. 40, No. 3, (2002), 536-545.

Butter, Christian, "Effect of Resynchronization Therapy Stimulation Site on the Systolic Function of Heart Failure Patients", *Circulation* 104(25), (Dec. 18, 2001), 3026-3029.

Chen, H. H., et al., "Diastolic Heart Failure in the Community: Clinical Profile, Natural History, Therapy, and Impact of Proposed Diagnostic Criteria", *Journal of Cardiac Failure*, 8(5), (2002), 279-287.

Curtis, J. P., et al., "The Association of Left Ventricular Ejection Fraction, Mortality, and Cause of Death in Stable Outpatients With Heart Failure", *Journal of the American College of Cardiology*, 42(4), (2003), 736-742.

Ding, J., et al., "Cardiac Pacing Using Adjustable Atrio-Ventricular Delays", U.S. Appl. No. 11/049,181, filed Feb. 2, 2005, 35 pgs.

Kass, D. A., "Improved Left Ventricular Mechanics From Acute VDD Pacing in Patients With Dilated Cardiomyopathy and Ventricular Conduction Delay", *Circulation*, 99(12), (Mar. 30, 1999), 1567-1573.

Kawaguchi, M., "Quantitation of Basal Dyssynchrony and Acute Resynchronization from Left or Biventricular Pacing by Novel Echo-Contrast Variability Imaging", *Journal of the American College of Cardiology*, vol. 39, No. 12, (2002), 2052-2058.

Kerwin, W. F, "Ventricular Contraction Abnormalities in Dilated Cardiomypathy: Effect of Biventricular Pacing to Correct Interventricular Dyssynchrony", *Journal of the America College of Cardiology*, vol. 35, No. 5, (2000), 1221-1227.

Kim, H., et al., "Integrated MEMS for Pressure Transponder", *1997 International Conference on Solid State Sensors and Actuators. Transducers '97*, vol. 2., (Chicago, IL), (1997), 1011-1014.

Le Rest, Catherine, "Use of left ventricular pacing in heart failure: Evaluation by gated blood pool imaging", *Journal of Nuclear Cardiology*, vol. 6, No. 6, (Nov./Dec. 1999), 651-656.

Little, W. C., "Clinical Evaluation of Left Ventricular Diastolic Performance", *Progress in Cardiovascular Disease*, 32(4), (1990), 273-290.

Nelson, Gregory S, "Left ventricular or biventricular pacing improves cardiac function at diminished energy cost in patients with dilated cardiomyopathy and left bundle-branch block", *Circulation*, 102(25), (Dec. 19, 2000), 3053-3059.

Nelson, G. S, "Predictors of Systolic Augmentation From Left Ventricular Preexcitation in Patients with Dilated Cardiomyopathy and Intraventricular Conduction Delay", *Circulation*, 101, (Jun. 13, 2000), 2703-2709.

Prinzen, F. W, "Mapping of regional myocardial strain and work during ventricular pacing: experimental study using magnetic resonance imaging tagging", *Journal of the American College of Cardiology*, 33(6), (May 1999), 1735-1742.

Redfield, M. M., et al., "Burden of Systolic and Diastolic Ventricular Dysfunction in the Community", *JAMA*, 289(2), (2003), 194-202.

Ritter, P., et al., "A Built-In System Based on the Peak Endocardial Acceleration (PEA) for AV-Delay Optimization in DDDR Pacing", *PACE*, 20(5) (Part II), (Abstract of Paper presented at EUROPACE '97), (May 1997), p. 1567.

Sogaard, P., "Impact of Acute Biventricular Pacing on Left Ventricular Performance and Volumes in Patients with Severe Heart Failure: a tissue Doppler and three-dimensional echocardiographic study", *Cardiology*, 95, (2001), 173-182.

Stellbrink, C., "Impact of Cardiac Resynchronization Therapy Using Hemodynamically Optimized Pacing on Left Ventricular Remodeling in Patients With Congestive Heart Failure and Ventricular Conduction Disturbances", *Journal of the American College of Cardiology*, vol. 38, No. 7, (Dec. 2001), 1957-1965.

Watanabe, M., et al., "Developmental Remodeling and Shortening of Cardiac Outflow Tract Involves Myocyte Programmed Cell Death", *Development*, 125 (19), (1998), 3809-3820.

Xiao, H. B, "Differing effects of right ventricular pacing and left bundle branch on left ventricular function", *British Heart Journal*, vol. 69, No. 2, (Feb. 1993), 166-173.

Yu, C.-M., et al., "High Prevalence of Left Ventricular Systolic and Diastolic Asynchrony in Patients With Congestive Heart Failure and Normal QRS Duration", *Heart*, vol. 89, (2003), 54-60.

Yu, C.-M., "Tissue Doppler Echocardiographic Evidence of Reverse Remodeling and Improved Synchronicity by Simultaneously Delaying Regional Contraction After Biventricular Pacing Therapy in Heart Failure", *Circulation*, 105, (2002), 438-445.

Zile, M. D., M. R., et al., "Diastolic Heart Failure: Diagnosis and Treatment", *Clinical Cornerstone*, 3(2), © 2000 Excerpta Medical, Inc., [online] [retrieved Jul. 16, 2001]. Retrieved from the Internet: <URL: http://cardiology.medscape.com/ExcerptaMed/ClinCornerstne/200.../pnt-clc0302.03.zile.htm>, 14 pgs.

"U.S. Appl. No. 10/703,398, Final Office Action mailed Aug. 6, 2009", 12 Pgs.

* cited by examiner

PACING THERAPY FOR DIASTOLIC HEART FAILURE

CROSS-REFERENCE TO RELATED APPLICATIONS

This application is related to co-pending, commonly assigned U.S. patent application Ser. No. 10/038,936, "METHOD AND APPARATUS FOR MEASURING LEFT VENTRICULAR PRESSURE," filed on Jan. 4, 2002, U.S. patent application Ser. No. 10/314,910, "METHOD AND APPARATUS FOR OPTIMIZING VENTRICULAR SYNCHRONY DURING DDD RESYNCHRONIZATION THERAPY USING ADJUSTABLE ATRIO-VENTRICULAR DELAYS," filed on Dec. 9, 2002, U.S. patent application Ser. No. 10/314,899, "METHOD AND APPARATUS FOR OPTIMIZING STROKE VOLUME DURING DDD RESYNCHRONIZATION THERAPY USING ADJUSTABLE ATRIO-VENTRICULAR DELAYS," filed on Dec. 9, 2002, U.S. patent application Ser. No. 10/402,324, "METHOD AND APPARATUS FOR QUANTIFICATION OF CARDIAC WALL MOTION ASYNCHRONY," filed on Mar. 28, 2003, and U.S. patent application Ser. No. 10/703,398, "ELECTRICAL THERAPY FOR DIASTOLIC DYSFUNCTION," filed on Nov. 7, 2003, all assigned to Cardiac Pacemakers, Inc., which are hereby incorporated by reference.

TECHNICAL FIELD

This document relates generally to cardiac rhythm management devices and, in particular, to the use of such devices in heart failure patients.

BACKGROUND

Heart failure (HF) is a debilitating global disease whose incidence is increasing dramatically. Heart failure refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Heart failure can be treated with a drug regimen designed to augment cardiac function or by pacing therapy. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

The treatments for HF discussed above are most appropriately used to treat patients with systolic dysfunction. In such patients, the fraction of the blood accumulated during diastolic filling of one or both ventricles that is pumped out during systole, referred to as the ejection fraction, is below normal. Recent epidemiological reports, however, have documented that a large percentage of HF patients maintain a normal left ventricular ejection fraction (EF)$\geq$50%. Although current treatment modalities have improved prognosis among individuals with a depressed EF, the application of these therapeutic strategies to the condition of HF with a normal EF have not had such favorable outcomes

SUMMARY

Described herein are methods and systems for delivering pacing therapy to HF patients who do not exhibit a reduced EF. Such patients do not have systolic dysfunction and generally do not benefit from established HF therapies that either augment contractile function or counteract conduction abnormalities. In one embodiment, a HF patient with a normal EF is tested for the adequacy of heart rate response during exercise. If the patient is found to be chronotropically incompetent, a rate-adaptive pacing mode is employed in order improve functional capacity. The rate-adaptive pacing mode may be employed with any appropriate pacing configuration including conventional bradycardia pacing to an atrium and/or ventricle, CRT, or pacing designed to improve diastolic function (e.g., ventricular septal pacing). In order to prevent the rate-adaptive pacing mode from unduly compromising diastolic filling in patients with diastolic dysfunction, one or more rate-adaptive pacing parameters are adjusted in accordance with an evaluation of the patient's diastolic function as the heart rate is increased. Such evaluation of the patient's diastolic function may be performed clinically with the appropriately adjusted rate-adaptive pacing parameters then being programmed into the pacing system. Alternatively, evaluation of diastolic function and adjustment of the rate-adaptive pacing parameters may be performed by the pacing system automatically.

In one embodiment, a cardiac pacing system includes a sensing circuit, a pacing circuit, a diastolic performance sensor, a signal processor, and a pacing controller. The diastolic performance sensor senses a signal indicative of a diastolic function. The signal processor receives and processes the signal indicative of the diastolic function, and includes a diastolic performance parameter generator that produces a diastolic performance parameter based on the signal indicative of the diastolic function. The pacing controller receives the diastolic performance parameter and adjusts one or more rate-adaptive pacing parameters in accordance with the diastolic performance parameter.

DETAILED DESCRIPTION

Figure 1A:
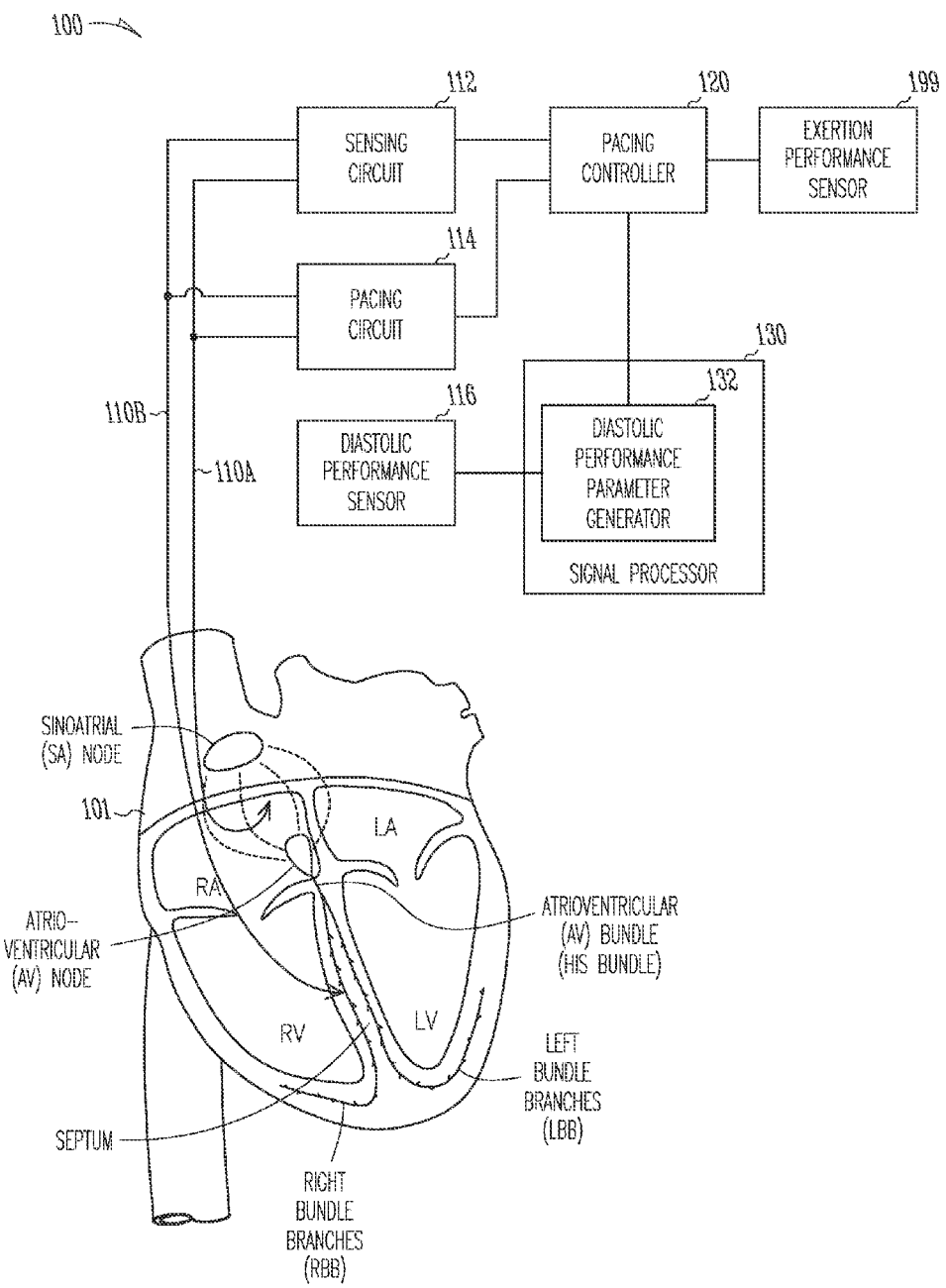
FIG. 1A is a schematic/block diagram illustrating one embodiment of a cardiac pacing system for treating the diastolic dysfunction and portions of an environment in which the system is used.

Although the mechanisms of HF with a normal EF are incompletely understood, diastolic dysfunction is thought to be a central component. The increasing recognition that HF may arise in the absence of significant systolic dysfunction has lead to the use of the term diastolic heart failure (DHF) when describing patients who exhibit HF and a normal EF. The term DHF will be used similarly herein.

Rate-adaptive pacing (RAP) has been demonstrated to improve response to physical activity in patients with inadequate chronotropic response, and improvements are most pronounced in patients who are chronotropically incompetent. Chronotropic incompetence (CI) is clinically defined as an attenuated exercise heart rate response, commonly perceived as an inability to achieve a predetermined percentage of predicted maximal heart rate, and is diagnosed through various types of exercise stress tests. The benefit of RAP, in conjunction with cardiac resynchronization therapy, on exercise performance has also been demonstrated in HF patients with a reduced EF and CI (See Tse, H. F., et al., *The incremental benefit of rate-adaptive pacing on exercise performance during cardiac resynchronization therapy*. J Am Coll Cardiol, 2005. 46(12): p. 2292-7). A severely blunted heart rate response (as attenuated peak heart rate and diminished heart rate acceleration) to incremental cycle exercise has also been observed in patients with HF and a normal EF (See Borlaug, B., Melenovsky, V., Shively, L., Swiger, K., and Kass, D A., *Impaired Systolic and Vasodilator Reserve in Patients with Heart Failure and a Normal Ejection Fraction*, in American Heart Association Scientific Sessions. 2005: Dallas, Tex.).

Described herein are methods and systems for treating DHF patients with pacing therapy in which such patients are identified by measurement of EF and/or evaluation of diastolic function. If a DHF patient is also found to have CI, a rate-adaptive pacing mode is employed to deliver the pacing therapy. The pacing therapy delivered in the RAP mode may be conventional bradycardia pacing to an atrium and/or ventricle, CRT, or pacing designed to improve diastolic function (e.g., ventricular septal pacing). An evaluation of diastolic function is performed on the patient to determine if such rate-adaptive pacing adversely affects diastolic filling of the ventricles. If the patient is found to have diastolic dysfunction, one or more rate-adaptive pacing parameters are adjusted in accordance with an evaluation of the patient's diastolic function as the heart rate is increased. The evaluation of the patient's diastolic function may be performed clinically with the appropriately adjusted rate-adaptive pacing parameters then being programmed into the pacing system. Alternatively, evaluation of diastolic function and adjustment of the rate-adaptive pacing parameters may be performed by the pacing system automatically. Described below are various embodiments of methods and systems for treating DHF patients with RAP, the features of which may be arbitrarily combined in any manner. The methods and systems described herein may also be combined in any manner with the methods and systems for delivering pacing therapy to treat diastolic dyssynchrony described in the aforementioned U.S. patent application Ser. No. 10/703,398.

1. Cardiac Pacing System

FIG. 1A is a schematic/block diagram illustrating one embodiment of a cardiac pacing system. In the illustrated embodiment, cardiac pacing system 100 includes leads 110A-B, a sensing circuit 112, a pacing circuit 114, a diastolic performance sensor 116, a signal processor 130, and a pacing controller 120. Leads 110A-B are intracardiac pacing leads each including one or more electrodes for sensing electrograms from and delivering pacing pulses to a predetermined region within a heart 101. Leads 110A-B provide for electrical connections between sensing circuit 112 and heart 101 and between pacing circuit 114 and heart 101. In one embodiment, diastolic performance sensor 116 is also incorporated into one of leads 110A-B for intracardiac placement. In the embodiment illustrated in FIG. 1, lead 110A is an atrial pacing lead with one or more electrodes for placement in the right atrium (RA) of heart 101, and lead 110B is a ventricular pacing lead with one or more electrodes for placement in the right ventricle (RV) and/or left ventricle (LV) of heart 101. The ventricular electrodes may be disposed to pace either septum or a free wall of the LV or RV. In other embodiments, cardiac pacing system 100 includes one or more pacing leads in additional to leads 110A-B to provide access to additional intracardiac regions, such as regions within the right RV and/or LV. In the embodiment illustrated in FIG. 1A, sensing circuit 112 senses RA and RV electrograms through leads 110A-B, and pacing circuit 114 delivers pacing pulses to the RV and/or LV through lead 110B. In other embodiments, where additional leads are included, sensing circuit 112 senses additional electrograms and, when necessary, pacing circuit 114 delivers pacing pulses to additional sites through the additional leads.

The controller 120 may be implemented as microprocessor that controls the overall operation of the device in accordance with programmed instructions stored in memory. The controller 120 interprets electrogram signals from the sensing circuit and controls the delivery of paces in accordance with a pacing mode. The sensing circuitry of the device generates atrial and ventricular electrogram signals from the voltages sensed by the electrodes of a particular sensing circuit. When an electrogram signal from an atrial or ventricular sensing circuit exceeds a specified threshold, the controller detects an atrial or ventricular sense, respectively, which pacing algorithms may employ to trigger or inhibit pacing. Bradycardia pacing modes are most commonly employed, whether to treat bradycardia or to deliver CRT. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected.

Patients with sinus node dysfunction (e.g, sinus bradyeardia, sinus arrest, paroxysmal supraventricular tachycardia alternating with periods of bradycardia or even asystole) may exhibit symptoms of their arrhythmias, and according to the *ACC/AHA/NASPE Guidelines for Implantation of Cardiac Pacemakers and Antiarrhythmia Devices*, such symptoms are essential in deciding whether a permanent pacemaker is indicated. Sinus node dysfunction may also express itself as chronotropic incompetence, resulting in exercise intolerance for the patient and limiting their ability to carry out normal physical activity.

In pacemaker patients who are chronotropically incompetent, atrial triggered pacing modes cannot be used (or relied upon) so the heart rate is determined solely by the pacemaker in the absence of intrinsic cardiac activity. That heart rate is determined by the programmed escape intervals of the pacemaker which cause paces to be delivered to the atria and/or ventricles, depending upon the pacing mode, if no intrinsic beats occur before expiration of the escape intervals. Pacing the heart at a fixed rate as determined by the length of the programmed escape intervals, however, does not allow the heart rate to increase with increased metabolic demand. It is for this reason that rate-adaptive pacemakers have been developed which vary the programmed escape intervals in accordance with one or more physiological parameters related to metabolic demand such as obtained from an accelerometer or minute ventilation sensor.

To provide rate-adaptive pacing capability, also interfaced to the controller is an exertion level sensor 199, which may be an accelerometer, a minute ventilation sensor, or other sensor that measures a parameter related to metabolic demand that indicates the body's need for an increased heart rate. The exertion level sensor 199 may also represent multiple exertion level sensing modalities. The exertion level sensor enables the controller to adapt the atrial and/or ventricular pacing rate in accordance with changes in the patient's physical activity in a rate-adaptive pacing mode. In a rate-adaptive pacing mode, one or more escape intervals are adjusted in accordance with a measured exertion level so that the pacing rate varies with metabolic demand. The modified pacing rate dictated by a rate-adaptive algorithm is referred to as the sensor-indicated rate. The rate-adaptive algorithm calculates the sensor-indicated rate by mapping a measured exertion level to a particular heart rate in accordance with a rate response function. In the case of a linear function, the response factor is the slope of the rate response curve. Various pacing parameters may be specified for a particular rate-adaptive pacing mode including the type of rate-response function, slope(s) of the rate-response curve, location of breakpoints that vary the slope of the rate-response curve, and a maximum heart rate.

The embodiment illustrated in FIG. 1A also includes a diastolic performance sensor that 116 senses a signal indicative of a diastolic function and a signal processor 130 that processes the sensed signal. The signal processor 130 may be a separate hardware component from the controller 120 or implemented as a part thereof. In one embodiment, signal processor 130 includes a diastolic performance parameter generator 132 to produce the diastolic performance parameter based on the signal indicative of the diastolic function.

In one embodiment, diastolic performance sensor 116 includes a pressure sensor to sense a signal indicative of an LV pressure. In one specific embodiment, diastolic performance sensor 116 is placed in the LV to directly sense the LV pressure. In other embodiments, diastolic performance sensor 116 indirectly senses the LV pressure, by sensing another pressure having a known or predictable relationship with the LV pressure. Examples of pressures having known or predictable relationships with the LV pressure during all or a portion of the cardiac cycle include an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety. In one embodiment, diastolic performance parameter generator 132 includes a diastolic pressure detector to detect a left ventricular end diastolic pressure (LVEDP) from the signal indicative of the LV pressure. The diastolic performance parameter is the LVEDP. In another embodiment, diastolic performance parameter generator 132 includes a diastolic pressure timer to measure a time constant (tau) related to a decrease in the left ventricular pressure. The diastolic performance parameter is that time constant.

In another embodiment, diastolic performance sensor 116 includes a pulmonary flow sensor to sense a signal indicative of a pulmonary venous blood flow. In one specific embodiment, the pulmonary flow sensor includes a pulmonary impedance sensing circuit to sense the pulmonary impedance, indicative of the pulmonary blood volume. Diastolic performance parameter generator 132 includes a velocity detector to calculate an antegrade pulmonary venous blood velocity based on the signal indicative of the pulmonary venous blood flow. The diastolic performance parameter is the pulmonary venous blood velocity.

In another embodiment, diastolic performance sensor 116 includes a mitral flow sensor to sense a signal indicative of blood flow through the mitral valve. In one specific embodiment, the mitral flow sensor includes an impedance sensor to a measure an LV volume. The LV volume is derived from an impedance measured between electrodes in the right ventricle and in a left ventricular coronary vein. One example of such an impedance sensor and measurement is discussed in U.S. Pat. No. 6,278,894, "MULTI-SITE IMPEDANCE SENSOR USING CORONARY SINUS/VEIN ELECTRODES," assigned to Cardiac Pacemakers, Inc., which is hereby incorporated by reference in its entirety. The time-derivative of this LV volume signal during diastole (after the opening of the mitral valve at the end of ejection) is a measure of the blood flow through the mitral valve. The peak blood flow during diastole, the duration of the rapid initial blood flow during diastole, and the time constant of the decrease in the blood flow during diastole are all useful measures of diastolic performance. Diastolic performance parameter generator 132 includes one or more of a peak detector to detect the peak blood flow, a timer to measure the duration of the rapid initial blood flow, and another timer to measure the time constant of the decrease in the blood flow. The diastolic performance parameter includes one of the peak blood flow, the duration of the rapid initial blood flow, and the time constant of the decrease in the blood flow during diastole.

In another embodiment, diastolic performance sensor 116 includes an acoustic sensor to sense a signal indicative of heart sounds. In one specific embodiment, the acoustic sensor includes an accelerometer. In another specific embodiment, the acoustic sensor includes a microphone. Diastolic performance parameter generator 132 includes a heart sound analyzer to detect a diastolic acoustic noise from the signal indicative of heart sounds. The diastolic performance parameter is the diastolic acoustic noise. The diastolic acoustic noise is the total acoustic noise measured over the diastolic phase of one cardiac cycles. Examples of methods for calculating the total acoustic noise measured over a predetermined time period are discussed in U.S. Pat. No. 6,044,298, "OPTIMIZATION OF PACING PARAMETERS BASED ON MEASUREMENT OF INTEGRATED ACOUSTIC NOISE," and U.S. Pat. No. 6,058,329, "OPTIMIZATION OF PACING PARAMETERS BASED ON MEASUREMENT OF ACOUSTIC NOISE," both assigned to Cardiac Pacemakers, Inc., which are hereby incorporated by reference in their entirety.

Figure 1B:
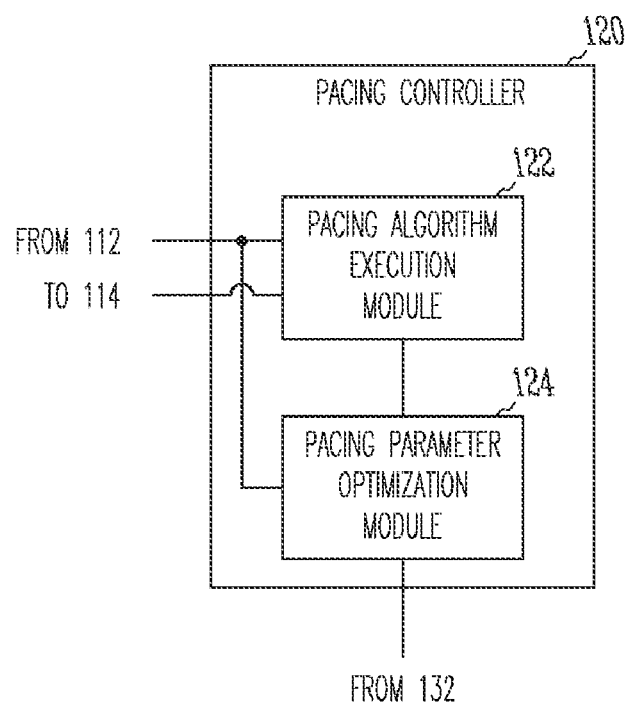
FIG. 1B is a schematic/block diagram illustrating one embodiment of a pacing controller of the cardiac pacing system of FIG. 1A.

FIG. 1B is a schematic/block diagram illustrating one embodiment of pacing controller 120. Pacing controller 120 receives the diastolic performance parameter and uses it to determine and/or adjust one or more pacing parameters. Pacing controller 120 includes a pacing parameter optimization module 124 and a pacing algorithm execution module 122. Pacing parameter optimization module 124 receives the diastolic performance parameter and calculates one or more approximately optimal pacing parameters based on at least the diastolic performance parameter. In one embodiment, the approximately optimal pacing parameter is a pacing parameter predicted to provide a target value (including a maximum or minimum value) for the diastolic performance parameter. In another embodiment, the approximately optimal pacing parameter is a pacing parameter predicted to maintain a threshold value for the diastolic performance parameter. In one specific embodiment, the target or threshold value for the diastolic performance parameter is determined based on systemic considerations including both systolic and diastolic performance of heart 101. As described below, the pacing parameter optimization module 124 adjusts the rate-adaptive pacing algorithm in a manner so as not to unduly compromise diastolic function. In one embodiment, the pacing controller is programmed to adjust one or more rate-adaptive pacing parameters in accordance with the diastolic performance parameter. The pacing controller may be further programmed to adjust one or more rate-adaptive pacing parameters if a comparison of the diastolic performance parameter with a specified threshold value indicates diastolic filling is unduly compromised. In another embodiment, the pacing controller is further programmed to adjust one or more rate-adaptive pacing parameters in a manner that maximizes diastolic performance, either continuously or intermittently according to a defined schedule.

In another embodiment, pacing parameter optimization module 124 includes a pacing site selector to select one or more pacing sites and a pacing timing calculator to calculate one or more pacing timing parameters such as atrioventricular and interventricular pacing delays. Pacing algorithm execution module 122 controls the delivery of the pacing pulses by executing a predetermined pacing algorithm using the one or more approximately optimal pacing parameters. In one embodiment, the predetermined pacing algorithm defines an atrial tracking pacing mode such as a DDD or a VDD mode. The one or more approximately optimal pacing parameters include an atrioventricular pacing delay. In one embodiment, wherein multiple ventricular leads are applied to provide sensing and pacing of multiple ventricular sites, the one or more approximately optimal pacing parameters include one or more atrioventricular pacing delays, one or more interventricular pacing delays, and/or one or more pacing sites to which pacing pulses are actually delivered.

Figure 2:
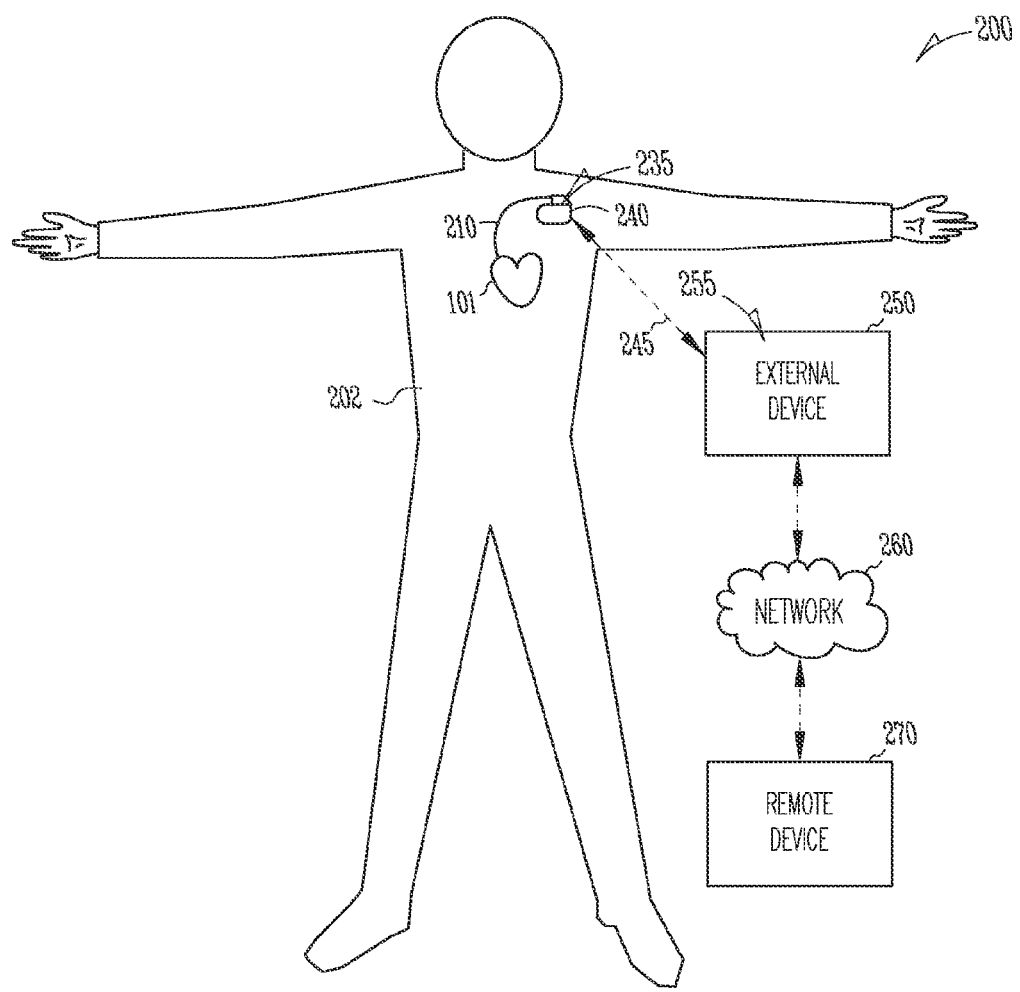
FIG. 2 is a schematic/block diagram illustrating one embodiment of portions a cardiac rhythm management (CRM) system including the cardiac pacing system of FIG. 1A and portions of an environment in which the CRM system is used.

FIG. 2 is a schematic/block diagram illustrating one embodiment of portions of a cardiac rhythm management (CRM) system 200 and portions of the environment in which system 200 is used. CRM system 200 incorporates cardiac pacing system 100 to provide a pacing therapy to heart 101. In one embodiment, CRM system 200 includes an implantable system 235, an external system 255, and a telemetry link 245 providing for bidirectional communication between implantable system 235 and external system 255. Implantable system 235 includes an implantable device 240 and a lead system 210. Implantable device 240 is implanted within a body 202 and coupled to heart 101 via lead system 210. Examples of implantable device 240 include pacemakers, pacemaker/defibrillators, cardiac resynchronization devices, cardiac remodeling control devices, and any other implantable medical devices with a pacing function. In one embodiment, lead system 210 includes leads 110A-B and additional pacing leads, if any. In another embodiment, diastolic performance sensor 116 is incorporated in a lead of lead system 210. In one embodiment, external system 255 is a patient management system including an external device 250 in proximity of implantable device 240, a remote device 270 in a relatively distant location, and a telecommunication network 260 linking external device 250 and remote device 270. An example of such a patient management system is discussed in U.S. patent application Ser. No. 10/323,604, "ADVANCED PATIENT MANAGEMENT FOR DEFINING, IDENTIFYING AND USING PREDETERMINED HEALTH-RELATED EVENTS," filed on Dec. 18, 2002, assigned to Cardiac Pacemakers, Inc., which is incorporated herein by reference in its entirety. The patient management system allows access to implantable system 235 from a remote location, for purposes such as monitoring patient status and adjusting therapies. In another embodiment, external system 255 includes a programmer. In one embodiment, telemetry link 245 is an inductive telemetry link. In an alternative embodiment, telemetry link 245 is a far-field radio-frequency telemetry link. In one embodiment, telemetry link 245 provides for data transmission from implantable device 240 to external system 255. This may include, for example, transmitting real-time physiological data acquired by implantable device 240, extracting physiological data acquired by and stored in implantable device 240, extracting therapy history data stored in implantable device 240, and extracting data indicating an operational status of implantable device 240 (e.g., battery status and lead impedance). In a further embodiment, telemetry link 245 provides for data transmission from external system 255 to implantable device 240. This may include, for example, programming implantable device 240 to acquire physiological data, programming implantable device 240 to perform at least one self-diagnostic test (such as for a device operational status), programming implantable device 240 to alter therapy parameters and programming implantable device 240 to deliver at least one therapy.

The physical distribution of cardiac pacing system 100 in CRM system 200 depends on practical factors such as the size and power constraints for an implantable device, computational power of the implantable device, and convenience of implementation and use. In one embodiment, cardiac pacing system 100 is included in implantable system 235. This embodiment allows for a diastolic performance based feedback loop (including diastolic performance sensor 116, signal processor 130, pacing controller 120, and pacing circuit 114) to operate continuously, without the need to communicate with external system 255. In another embodiment, portions of cardiac pacing system 100 are included in implantable system 235, and the remaining portions are included in external system 255. In one specific embodiment, external system 255 includes diastolic performance parameter generator 132 and pacing parameter optimization module 124. The signal sensed by diastolic performance sensor 116 is transmitted to external system 255 via telemetry link 245. One or more approximately optimal pacing parameters are transmitted to implantable device 240 via telemetry 245. Including portions of cardiac pacing system 100 in external system reduces size, power, and/or computational demands on implantable device 240.

2. Rate-Adaptive Pacing in HF Patients

A patient with symptomatic heart failure may first be identified as having diastolic heart failure by measurement of his or her ejection fraction. If the patient is also found to be chronotropically incompetent, the patient is treated with pacing therapy using a rate-adaptive pacing mode. An evaluation of the patient's diastolic function may then be performed. Diastolic dysfunction may involve dyssynchronous relaxation of the ventricles and/or a non-compliant ventricle due to many causes. At higher heart rates brought about by rate-adaptive pacing, the ventricles may not have time to fill adequately if diastolic dysfunction is present. Such lessened diastolic filling would then lessen cardiac output. Therefore, if the patient is found to also exhibit diastolic dysfunction, a determination is made as to whether the rate-adaptive pacing adversely affects cardiac function at higher heart rates by compromising diastolic filling. If so, one or more rate-adaptive pacing parameters are adjusted in accordance with a sensed diastolic performance parameter so that diastolic filling is not unduly compromised.

Figure 3:
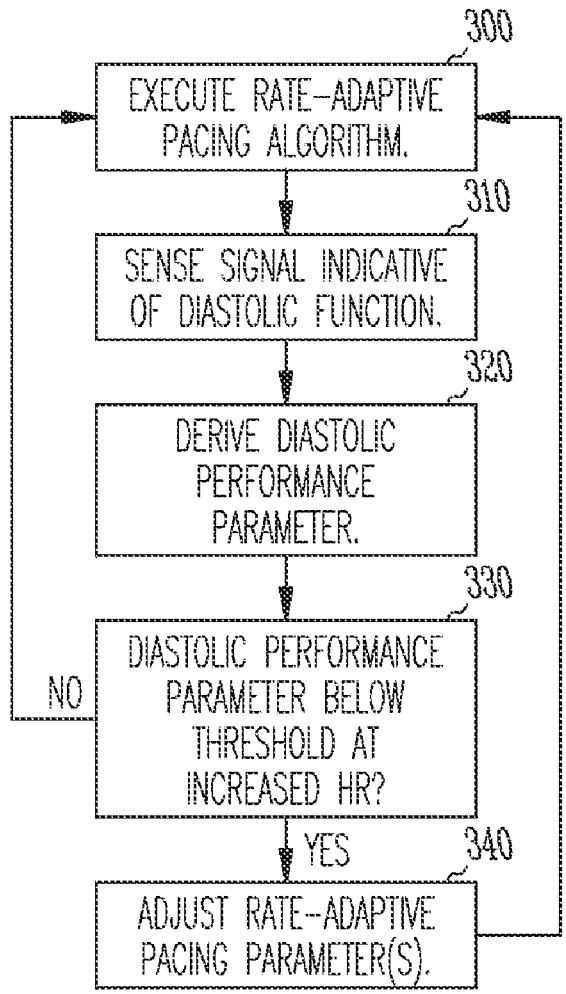
FIG. 3 is a flow chart illustrating one embodiment of a method for controlling rate-adaptive pacing in a diastolic heart failure patient.

FIG. 3 is a flow chart illustrating one embodiment of a method for improving diastolic performance by cardiac pacing. The method determines and adjusts one or more rate-adaptive pacing parameters based on a sensed signal indicative of a diastolic function. Such rate-adaptive pacing parameters may include maximum heart rate, a slope of the rate response curve, type of rate response function, and cessation or initiation of rate adaptive pacing. In one embodiment, the sensed signal indicative of diastolic function is obtained in a clinical setting by appropriate instrumentation and may include any of the diastolic performance parameters discussed above as well as other modalities appropriate for evaluating diastolic function such as echocardiography. In another embodiment, the method is performed by a cardiac pacing system such as described above in a closed-loop manner.

A rate-adaptive pacing algorithm to deliver pacing therapy is executed at 300. The pacing therapy may be conventional bradycardia pacing, CRT, or pacing designed to treat diastolic dysfunction by pre-excitation of the ventricular septum. A signal indicative of the diastolic function is sensed at 310, and a diastolic performance parameter is derived from that signal at 320. In one embodiment, the signal indicative of the diastolic function is a signal indicative of an LV pressure, and the diastolic performance parameter is an LVEDP measured from the signal indicative of the LV pressure. In another embodiment, the signal indicative of the diastolic function is a signal indicative of an LV pressure, and the diastolic performance parameter is a minimum left ventricular pressure measured from the signal indicative of the LV pressure. In another embodiment, the signal indicative of the diastolic function is a signal indicative of an LV pressure, and the diastolic performance parameter is an LVEDP measured from the signal indicative of the LV pressure. In another embodiment, the signal indicative of the diastolic function is a signal indicative of an LV pressure, and the diastolic performance parameter is a diastasis pressure measured from the signal indicative of the LV pressure immediately before left atrial systole. In another embodiment, the signal indicative of the diastolic function is a signal indicative of an LV pressure, and the diastolic performance parameter is a time constant (tau) related to a decrease in the LV pressure. In another embodiment, the signal indicative of the diastolic function is a signal indicative of pulmonary arterial pressure and the performance parameter is a pulmonary arterial diastolic pressure. In another embodiment, the signal indicative of the diastolic function is a signal indicative of a pulmonary venous blood flow, and the diastolic performance parameter is an antegrade pulmonary venous blood velocity calculated based on the signal indicative of the pulmonary venous blood flow. In another embodiment, the signal indicative of the diastolic function is a signal indicative of blood flow through the mitral valve, and the diastolic performance parameter is the peak blood flow, the duration of the initial blood flow peak, a time constant related to the decrease in the blood flow during early diastole or a ratio between peak blood flow in early and late diastole. In another embodiment, the signal indicative of the diastolic function is a signal indicative of heart sounds, and the diastolic performance parameter is a diastolic acoustic noise detected from the signal indicative of heart sounds. Other examples of signals indicative of diastolic function are: LA pressure, PA pressure, stroke volume, atrial pressure, and mechanical properties of the inter-ventricular septum such as a strain gauge measurement of contractile force. In another embodiment, the signal indicative of the diastolic function is a signal indicative of an LV volume, and the diastolic performance parameter is a peak derivative of the LV volume, occurring during diastole and indicative of peak blood flow into the heart. In another embodiment, the signal indicative of the diastolic function is a signal indicative of an LV volume, and the diastolic performance parameter is a total LV volume change during diastole.

As the patient's heart rate is varied due to the rate-adaptive pacing (either during exercise testing or during everyday activities), the diastolic performance parameter is compared with a specified threshold value. The specified threshold value would be different for each particular diastolic performance parameter and may be determined for an individual patient empirically by correlating the value of the diastolic performance parameter with stroke volume. The threshold value may also be a long term average of the performance parameter or an average measured under specified conditions, such as when the patient is at rest as indicated by heart rate or such parameter. If the diastolic performance parameter is found to be below threshold at an increased HR at 330, one or more rate-adaptive pacing parameters are adjusted at 340. (This assumes that the diastolic performance parameter decreases with worsening diastolic function. A diastolic performance parameter could also be defined oppositely.) Otherwise, the rate-adaptive pacing mode continues without adjustment. The steps may be repeated until the rate-adaptive pacing mode results in a diastolic performance parameter that remains above the specified threshold.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac pacing system comprising:
   a sensing circuit to sense at least one cardiac signal;
   a pacing circuit to deliver pacing pulses;
   an exertion level sensor;
   a diastolic performance sensor to sense a signal indicative of a diastolic function that relates to how optimally the ventricles are filling with blood during diastole;
   a signal processor adapted to receive and process the signal indicative of the diastolic function, the signal processor including a diastolic performance parameter generator to produce a diastolic performance parameter based on the signal indicative of the diastolic function;
   a pacing controller coupled to the sensing circuit and the pacing circuit, the pacing controller being programmed to deliver paces with a rate-adaptive pacing mode based upon signals from the exertion level sensor wherein a rate-adaptive algorithm maps the exertion level signals to a modified pacing rate in accordance with a rate-response function;
   wherein the pacing controller is programmed to determine if diastolic filling is compromised by comparing the diastolic performance parameter with a specified threshold value; and
   wherein the pacing controller is further programmed to adjust one or more rate-adaptive pacing parameters that define the rate-response function if a comparison of the diastolic performance parameter with a specified threshold value indicates diastolic filling is compromised, wherein the one or more rate-adaptive pacing parameter are adjusted in a manner that tends to prevent increases in the modified pacing rate which compromise diastolic filling.

2. The cardiac pacing system of claim 1 wherein the pacing controller is further programmed to adjust one or more rate-adaptive pacing parameters in a manner that maximizes diastolic performance.

3. The cardiac pacing system of claim 1 wherein the rate-adaptive pacing parameter adjusted by the pacing controller is a maximum heart rate.

4. The cardiac pacing system of claim 1 wherein the rate-adaptive pacing parameter adjusted by the pacing controller is a slope of a rate response curve.

5. The cardiac pacing system of claim 1 wherein the rate-adaptive pacing parameter adjusted by the pacing controller results in cessation of rate-adaptive pacing.

6. The cardiac pacing system of claim 1 wherein the diastolic performance sensor comprises a pressure sensor to sense a signal indicative of a left ventricular pressure.

7. The cardiac pacing system of claim 6 wherein the pressure sensor comprises a left ventricular pressure sensor.

8. The cardiac pacing system of claim 6 wherein the pressure sensor comprises a left atrial pressure sensor.

9. The cardiac pacing system of claim 6 wherein the pressure sensor comprises a coronary vein pressure sensor.

10. The cardiac pacing system of claim 6 wherein the pressure sensor comprises a pulmonary arterial pressure sensor.

11. The cardiac pacing system of claim 1 wherein the diastolic performance parameter generator comprises a diastolic pressure detector to detect a left ventricular end diastolic pressure from the signal indicative of the left ventricular pressure.

12. The cardiac pacing system of claim 1 wherein the diastolic performance parameter generator comprises a diastolic pressure detector to detect a pulmonary arterial diastolic pressure from the signal indicative of pulmonary arterial pressure.

13. The cardiac pacing system of claim 1 wherein the diastolic performance parameter generator comprises a diastolic pressure timer to measure a time constant related to a decrease in the left ventricular pressure.

14. The cardiac pacing system of claim 1 wherein the diastolic performance sensor comprises a flow sensor to sense a signal indicative of a blood flow.

15. The cardiac pacing system of claim 14 wherein the flow sensor comprises an impedance sensing circuit.

16. The cardiac pacing system of claim 14 wherein the flow sensor includes a pulmonary blood flow sensor adapted to sense a signal indicative of a pulmonary venous blood flow.

17. The cardiac pacing system of claim 14 wherein the diastolic performance parameter generator comprises a velocity detector to calculate an antegrade pulmonary venous blood velocity based on the signal indicative of the pulmonary venous blood flow.

18. The cardiac pacing system of claim 14 wherein the flow sensor includes a mitral blood flow sensor adapted to sense a signal indicative of a blood flow through a mitral valve.

19. The cardiac pacing system of claim 18 wherein the diastolic performance parameter generator comprises a peak detector to detect a peak blood flow from the signal indicative of the blood flow through the mitral valve.

20. The cardiac pacing system of claim 14 wherein the diastolic performance parameter generator comprises a timer to measure a duration of a rapid initial blood flow from the signal indicative of the blood flow through the mitral valve.

21. The cardiac pacing system of claim 14 wherein the diastolic performance parameter generator comprises a timer to measure a time constant related to a decrease in the blood flow through the mitral valve from the signal indicative of the blood flow through the mitral valve.

22. The cardiac pacing system of claim 14 wherein the diastolic performance parameter generator comprises a timer to measure a ratio of the peak of initial blood flow and late blood flow from the signal indicative of the blood flow through the mitral valve.

23. The cardiac pacing system of claim 1 wherein the diastolic performance sensor comprises a volume sensor indicative of left ventricular volume.

24. The cardiac pacing system of claim 15 wherein the volume sensor comprises an impedance sensing circuit.

25. The cardiac pacing system of claim 23 wherein the diastolic performance parameter generator comprises a peak detector to detect a total change in LV volume during diastole.

26. The cardiac pacing system of claim 1 wherein the diastolic performance sensor comprises an acoustic sensor to sense a signal indicative of heart sounds.

27. The cardiac pacing system of claim 26 wherein the acoustic sensor comprises an accelerometer.

28. The cardiac pacing system of claim 26 wherein the acoustic sensor comprises a microphone.

29. The cardiac pacing system of claim 26 wherein the diastolic performance parameter generator comprises a heart sound analyzer to detect a diastolic acoustic noise from the signal indicative of heart sounds.

30. The cardiac pacing system of claim 1 wherein the pacing controller further programmed to adjust the atrioventricular delay during dual chamber or biventricular pacing in accordance with the diastolic performance parameter.

31. The cardiac pacing system of claim 1 wherein the pacing controller further programmed to adjust the interventricular delay during biventricular pacing in accordance with the diastolic performance parameter.

32. A method for treating a patient with diastolic heart failure, comprising:
    implanting a pacing system in the patient;
    programming the pacing system to deliver pacing therapy in a rate-adaptive mode wherein a rate-adaptive algorithm maps the exertion level signals to a modified pacing rate in accordance with a rate-response function;
    measuring a diastolic performance parameter during heart rate changes brought about by the rate-adaptive pacing therapy, wherein the diastolic performance parameter relates to how optimally the ventricles are filling with blood during diastole;
    determining if diastolic filling is compromised by comparing the diastolic performance parameter with a specified threshold value; and,
    adjusting one or more rate-adaptive pacing parameters that define the rate-response function if a comparison of the diastolic performance parameter with a specified threshold value indicates diastolic filling is unduly compromised, wherein the one or more rate-adaptive pacing parameter are adjusted in a manner that tends to prevent increases in the modified pacing rate which compromise diastolic filling.

33. The method of claim 32 further comprising adjusting one or more rate-adaptive pacing parameters in a manner that maximizes diastolic performance.

34. The method of claim 32 wherein the rate-adaptive pacing parameter is a maximum heart rate.

35. The method of claim 32 wherein the rate-adaptive pacing parameter adjusted is a slope of a rate response curve.

* * * * *